(12) United States Patent
Garuti, Jr. et al.

(10) Patent No.: US 8,007,584 B2
(45) Date of Patent: Aug. 30, 2011

(54) COMPOSITIONS FOR USE IN CONSTRUCTION AND METHODS OF APPLYING THE SAME

(75) Inventors: John Garuti, Jr., New York, NY (US); Louis M. Calvo, Bayshore, NY (US)

(73) Assignee: Formulated Solutions, LLC, Woodside, NY (US)

( * ) Notice: Subject to any disclaimer, the term of this patent is extended or adjusted under 35 U.S.C. 154(b) by 657 days.

(21) Appl. No.: 12/228,060

(22) Filed: Aug. 8, 2008

(65) Prior Publication Data

US 2010/0034978 A1    Feb. 11, 2010

(51) Int. Cl.
*C04B 7/13* (2006.01)

(52) U.S. Cl. .......................... 106/713; 106/724; 106/727

(58) Field of Classification Search .................. 106/713, 106/724, 727
See application file for complete search history.

(56) References Cited

U.S. PATENT DOCUMENTS

| | | | |
|---|---|---|---|
| 3,197,313 A | 7/1965 | Greiner | |
| 4,065,319 A | 12/1977 | Desmarais | |
| 4,089,695 A | 5/1978 | Ray | |
| 4,373,956 A | 2/1983 | Rosskopf | |
| 4,501,617 A | 2/1985 | Desmarais | |
| 4,556,426 A | 12/1985 | Chesney, Jr. | |
| 4,661,160 A | 4/1987 | Novinson | |
| 5,654,012 A | 8/1997 | Lutey | |
| 5,747,578 A | 5/1998 | Schmitz et al. | |
| 5,753,036 A | 5/1998 | Hornaman et al. | |
| 5,763,508 A | 6/1998 | Hess et al. | |
| 6,046,269 A | 4/2000 | Nass | |
| 6,132,777 A | 10/2000 | Lutey | |
| 6,241,815 B1 | 6/2001 | Bonen | |
| 6,585,813 B2 | 7/2003 | Kiik et al. | |
| 6,660,079 B2 | 12/2003 | Jodlbauer et al. | |
| 6,709,508 B2 | 3/2004 | Dietrich et al. | |
| 6,740,692 B2 | 5/2004 | Weitzel et al. | |
| 6,784,229 B2 | 8/2004 | Rooshenas | |
| 7,232,483 B2 | 6/2007 | Jardine et al. | |
| 2002/0162485 A1 | 11/2002 | Jodlbauer et al. | |
| 2003/0005861 A1 | 1/2003 | Dietrich et al. | |
| 2003/0221592 A1 | 12/2003 | Sironi et al. | |
| 2004/0175589 A1 | 9/2004 | Rabasco et al. | |
| 2006/0267234 A1 | 11/2006 | Ong et al. | |
| 2007/0027224 A1* | 2/2007 | Cowan et al. | 521/56 |

FOREIGN PATENT DOCUMENTS

| | | |
|---|---|---|
| BR | 9601518 A | 9/1997 |
| CN | 1277980 A | 12/2000 |
| DE | 2815223 A1 | 10/1979 |
| JP | 2006335597 A | 12/2006 |
| WO | WO2006094528 A1 | 9/2006 |

OTHER PUBLICATIONS

Shimizu, T; Aizawa, S.; Watanabe, H; Adachi, S.; "Mortar compositions containing alkali-resistant anti-mold agents" Chemical Abstracts, vol. 113, No. 14, 120011, Jan. 25, 1990, p. 301.
Database WPI Week 199751, Thomson Scientific, London, GB, AN 1997-550366 Katz De Castro, Egon: "Elastic adn water-repellant jointing cement for floorsand walls—contains Portland cement, sand and an additive mixture of cement and various chemicals".

* cited by examiner

*Primary Examiner* — Eisa Elhilo
(74) *Attorney, Agent, or Firm* — Dilworth & Barrese, LLP

(57) ABSTRACT

A composition for use in construction that is substantially free of volatile organic compounds (VOC) that when applied to a surface produces a smooth or textured, water-shedding (hydrophobic properties), aesthetically-pleasing, protective continuous coating. The coated surface as well as the method of preparing and applying the composition is also provided.

21 Claims, No Drawings

COMPOSITIONS FOR USE IN CONSTRUCTION AND METHODS OF APPLYING THE SAME

FIELD OF THE INVENTION

The invention relates to construction coating compositions for producing smooth and textured, substantially continuous protective surfaces as well as methods of coating a surface with the same. In particular, the present invention relates to a dry composition that when hydrated produces a finishing coating composition substantially free of volatile organic compounds (VOC) that when applied to a surface produces a smooth, water-shedding (hydrophobic), aesthetically-pleasing, protective continuous coating with state-of-the-art antimicrobial protection.

BACKGROUND OF THE INVENTION

Builders of both commercial and noncommercial buildings are constantly looking for new innovative products in order to make buildings more energy efficient, to better protect them from the weather as well as make the buildings more aesthetically pleasing.

Energy efficiency is directly related to thermal insulation. That is, the less energy lost to the surrounding environment by the building structure, the less energy required to heat the building. A well-insulated building leads to increased energy savings. As for weatherproofing, products that increase water shedding (hydrophobicity) enhance the weatherproofing of the building. However, numerous products on the market today that have improved thermal insulation as well as enhanced water shedding are not as aesthetically pleasing as less efficient products that are designed for this purpose. One product currently in use today in the building industry is stucco. Although stucco has some good qualities, it suffers from a number of very serious shortcomings.

That is, since stucco is made up almost exclusively of sand and cement, it is porous and quite pervious to moisture. This not only can lead to severe structural damage due to fungus and mildew formation when the underlying substrate is plywood or a similar material but can also lead to water damage of interior walls. In addition, the porous nature of stucco results in a loss of energy to the surrounding environment, which leads to, increased energy costs. In addition, stucco is a very rigid covering and offers only mediocre impact resistance. Rigidity is an especially undesirable characteristic when combined with moisture permeability and, for this reason, stucco has a limited life span when exposed to repeated freeze/thaw cycles because the water absorbed expands and contracts as it freezes and thaws and thus creates internal fractures in the stucco facing that grow and allow even more water to infiltrate through to the underlying substrate. Stucco is therefore not well suited for use in areas subject to freezing temperatures.

One way that these problems can be combated, is to apply water-sealing agents to the outer surface of the stucco finish. However, the sealants available on the market today that can be applied to a porous stucco finish are formulated as liquids and contain volatile organic compounds (VOC) that are not only harmful for the environment but create numerous health risks for workers applying these sealants. In addition, these sealants contain numerous organic materials that require the sealant to be shipped in liquid form instead of in a ready mix dry form, which drastically adds to the shipping costs associated with these products. Moreover, liquid sealants have strict storing and shipping requirements, present additional hazards when shipped, and have a limited shelf life due to possible chemical separation/break down of these liquid sealants.

Therefore, what is needed is a dehydrated composition that upon hydration can be applied to a porous surface in order to sufficiently fill in the pores, cracks, and crevices of the surface to be coated so as to create a water shedding (hydrophobic) finish having a strengthened, smooth esthetically pleasing surface. Also needed is a sealant that in addition to the aforementioned features can provide increased flexibility to the rather rigid stucco finish when applied. The increased flexibility will reduce cracking of a traditional stucco surface due to normal shifting of building material over time. The present invention provides such a composition as well as a method for applying the composition to a prepared surface. The composition and methods of the present invention are further discussed and described in the sections that directly follow.

SUMMARY OF THE INVENTION

The present invention is directed to a composition for use in construction that when applied to a prepared surface such as concrete, stucco, EIFS Base Coat and fiber-reinforced cement backer board, to name a few, seals, strengthens and provides an esthetically pleasing, water-shedding, microbial resistant smooth or textured, continuous coatings. The composition once applied to a surface as a coating has hydrophobic properties (water-shedding properties), which, in turn allows the coating to shed water and prevent infiltration of water pass the protective coating produced from the inventive composition.

That is, applying the composition of the present invention will transform a porous rough construction surface, such as a traditional stucco surface or concrete, into a surface in which all the pores and crevices are filled so as to provide a smooth, impervious, weather-resistant and antimicrobial coating. The compositions of the present invention which can be colored, include fungicides, biocides as well as a vast array of other additives as long as the additives do not produce substantial VOC's so as to be consistent with the zero (0) VOC objective of the present invention.

One objective of the present invention is to provide a composition having the aforementioned characteristics that can be stored as a dry composition until it is ready to be used at which time the composition can be mixed with water (usually on-site) and applied to a properly prepared surface. The claimed composition can be applied to the prepared surface using the method of the present invention. One embodiment of the present invention is directed to a composition comprising about 5 to about 95% by weight of dry cement with the remainder of the composition comprising particles having a bulk density equal to or greater than about 8 pounds/gal. The particles of the composition comprising about 0.10 to about 20% by weight of at least one dry thickening agent, about 0.10 to about 95.0% by weight of a particulate having an average particle size of about 10 microns to about 3 mm; and about 0.10 to about 10.0% by weight of an antimicrobial or biocide material wherein the sum of the dry cement and said particles does not exceed 100% by weight.

In another embodiment of the present invention the composition further comprises about 1 to about 90% by weight of at least one emulsion and/or re-dispersible powder polymer having an average particle size ranging from about 0.3 to about 9 microns wherein more than about 90% by volume of said emulsion and/or re-dispersible powder polymer particles are less than or equal to about 400 µm. This particulate size is key in producing a composition that can fill in all of the gaps, cracks, crevices and pores of the surface to which it is being applied.

Another objective of the present invention is to provide a method for coating a surface with the composition of the present invention as described above comprising preparing the surface for coating with the composition and then coating the surface with the composition. In one embodiment of the present invention, the surface is prepared by applying a primer to a substantially flat continuous surface to produce a primed surface and applying the composition of the present invention to the primed surface to produce a finished surface. Preparation of the surface to be coated is dependent on the condition and the material in which the surface to be coated is constructed. Accordingly, another embodiment of the method of the present invention comprises additional preparation steps of the surface to be coated. The method of the present invention may also include adhering at least one water-resistive and drainage barrier material to a surface to produce a protected surface, fastening a wire lath to the protected surface to produce a reinforced surface that creates a substrate offering mechanical bonding characteristics. Further preparation may include applying a construction grade material such as Portland cement stucco to the wire lath so as to produce a substantially flat continuous surface. It is to this flat substantially flat surface that the composition of the present invention is applied to produce a sealed, water shedding (hydrophobic properties), and strengthened, esthetically pleasing, smooth coating topcoat. The compositions and methods of the present invention are further described below.

Another objective of the present invention is to provide a method for coating a surface with the composition of the present invention directly onto the surface. That is, a method to provide the direct application of the coating of the invention to a surface without the use of the primer. The surface that may be coated using this method may be the Base Coat component of an EIFS (Exterior Insulating and Finishing System) application.

DETAILED DESCRIPTION OF THE INVENTION

The present invention provides a composition for use in construction that when applied to a surface provides a water repelling, strengthened, esthetically pleasing, smooth or textured coating topcoat. The composition can be applied to any prepared surface but is especially useful on surfaces that are brittle and porous and therefore suffer from cracking, insufficient water shedding (hydrophobic properties), low insulative properties and easy cracking. One such surface that suffers from many of these shortcomings is a traditional stucco surface known in the industry as three-coat or one-coat stucco.

Stucco or render is a material made of an aggregate, a portland cement binder and water. Stucco is applied wet and hardens to a very dense solid. It is used as a coating for walls and ceilings and for decoration. Stucco may be used to cover less visually appealing construction materials such as concrete, cinder block or clay brick and adobe, also known as CMU (cement masonry unit) but stucco itself is a very porous, non-smooth finish. Stucco is different than plaster and mortar. This difference is based more on use than composition. Until the later part of the nineteenth century, plaster was commonly used inside a building, while stucco was used outside. Traditional stucco consists of lime and sand (which are also used in mortar). Animal, plant or synthetic fibers were often added for additional strength. In the later part of the nineteenth century, modern stucco included Portland cement in an attempt to improve its durability. Portland cement is the most common type of cement and is a basic ingredient of concrete, mortar, as well as modern stucco.

Although modern stucco including Portland cement has increased durability over traditional stucco it is also more rigid. This rigidity produces a rough surface and compromises its ability to maintain an attractive exterior surface with the passage of time. It is well known that wall panels tend to shift during the life of the building due to settling and seasonal variations in temperature and the joints between the panels must therefore accommodate these movements. The traditional solution to this problem is to fill the joint with a caulking compound. However, both hard and soft curing caulking compounds tend to shrink or expand under these circumstances and cannot be depended upon to maintain the watertight seal they were intended to form. In addition, both types of caulk give rise to irregularities on the outer surface of the stucco coat around the joint areas such as cusps or depressions that significantly and permanently alter the outward appearance of the stucco finish. Another well-known problem is the formation upon curing of a discontinuity in appearance of the stucco coat across the face of the finished wall. This problem exhibits itself both across the face of individual wallboard panels and at the joint between juxtaposed panels. Another problem with stucco and other coatings in general, is that long-term antimicrobial protection does not exist. The present invention is designed so as to overcome this shortcoming as further described in the sections below.

Even with the many shortcomings of stucco, it is nevertheless, a very popular construction material. Although various solutions to these shortcomings have been proposed in the past, the composition of the present invention addresses many if not all of these shortcomings in a single thinly applied topcoat layer. That is, as further described below, the composition of the present invention when applied to a prepared surface using the method of the present invention produces, a sealed, water shedding (hydrophobic properties), strengthened, esthetically pleasing, uniform surface that corrects many of the shortcomings of stucco and similar coatings as discussed above. In particular, the present composition fills in the cracks and pores of the stucco surface to produce a uniform, textured appearance that seals the surface to increase its thermal retention and water-shedding or hydrophobic properties and long-term antimicrobial properties. The composition of the present invention also provides additional flexibility to the stucco or cementitious surface so reduce chipping and limit cracking due to settling of the building. Therefore, all in all the present composition remedies many if not all of the shortcomings of stucco by decreasing the cost associated with surfacing a building. This is also achieved without the potentially harmful VOC typically associated with acrylic based coatings.

The following discloses the specific components that are combined to produce the various embodiments of the dry mix composition of the present invention. Each component is identified by the generic name of the product or by a well-known trade name with the basic chemical formula (if available) for each component. The component name is used for ease and clarity of description. Although specific trade names and/or product names have been disclosed, the invention is not limited to those products, but should include any product that can be substituted for any of the recited component products.

The present invention is directed to a composition for use in construction comprising about 5 to about 95% by weight of dry cement, with the remainder of the composition comprising particles having a bulk density equal to or greater than about 8 pounds/gal. The particles of the composition comprising about 0.10 to about 95.0% by weight of a particulate having an average particle size of about 10 microns to about 3 mm. Additional embodiments of the present invention may contain about 5 to about 80% by weight of dry cement, about 15 to about 70% of dry cement, about 25 to about 65% of dry cement as well as numerous percentages in between. As with all of the embodiments of the present invention, the difference between the percentage of cement in the composition and 100% is made upon of the particles of the present invention.

The term "cement" in the context of this formulation is intended to include, but is not limited to: hydraulic, gypsum and alite cements, such as Portland Cement; blended cements; masonry cement; oil well cement; natural cement; alumina cement; expansive cements, and the like, and mixtures thereof.

It is preferred that the particles of the present composition be in the dry powdered form to allow for easy mixing with the rest of the components of the composition. Particles of the present invention may comprise about 0.10 to about 20% by weight of at least one dry thickening agent. In the alternative embodiments of the present invention the composition may contain about 1 to about 15% by weight of at least one thickening agent, about 5 to about 10% by weight of at least one thickening agent as well as numerous percentages in between. The thickening agents that may be used in the present invention include but are not limited to one or more polysaccharide plasticizers which can be further subdivided into cellulose based materials and derivatives thereof, starch based materials and derivatives thereof, and other polysaccharides. Suitable cellulose based rheology-modifying agents include, for example, methylhydroxyethylcellulose, hydroxymethylethylcellulose, carboxymethylcellulose, methylcellulose, ethylcellulose, hydroxyethylcellulose, hydroxyethylpropylcellulose, etc. The entire range of possible permutations is enormous and for practical purposes need not be listed. Nevertheless, it will be appreciated that many other cellulose materials have essentially the same or similar properties as those mentioned and are equivalent for the present purposes. Suitable starch based materials include, for example, amylopectin, amylose, sea-gel, starch acetates, starch hydroxyethyl ethers, ionic starches, long-chain alkylstarches, dextrins, amine starches, phosphate starches, and dialdehyde starches. Other natural polysaccharide based rheology-modifying agents include, for example, alginic acid, phycocolloids, agar, gum arabic, guar gum, welan gum, locust bean gum, gum karaya, and gum tragacanth, cellulose ether, modified cellulose ether, polyvinyl alcohol acetylated hydrophobically modified polyvinyl alcohol, and mixtures thereof. It is preferred that thickening agents used in the present invention be limited to non-VOC producing thickening agents upon re-hydration of the composition of the present invention with water.

The present composition may also contain about 0.10 to about 95.0% by weight of a particulate having an average particle size of about 10 microns to about 3 mm. In alternative embodiments of the present invention the composition may contain about 1 to about 80% by weight of at least one particulate, about 5 to about 65% by weight of at least one particulate, 20 to about 50% of at least one particulate as well as numerous percentages in between and mixtures thereof. The term "particulate" in the context of this formulation is intended to include, but is not limited to any type of course ground non-reactive particle including sand that is commonly used in the building industry, ground fiberglass, small beads glass beads, ground plastic, and mixtures thereof. Examples of suitable sands include ASTM 20/30 silica sands, dune sands, beach sands and job site sands.

The composition of the present invention may also contain about 0.10 to about 10.0% by weight of an antimicrobial and/or biocide material. In alternative embodiments of the present invention the composition may contain about 1 to about 6% by weight of an antimicrobial and/or biocide material, about 2 to about 4% by weight of an antimicrobial and/or biocide material, as well as numerous percentages in between. The terms "antimicrobial" and/or "biocide" in the context of this formulation is intended to include, but is not limited to fungicides, herbicides, insecticides, antimicrobial agents comprising sodium, potassium, calcium, zinc, copper, and barium salts of carbonate, silicate, sulfate, halide, and borate in all forms; zinc carboxylates; boric acids; sodium dichromate; copper chrome arsenate (CCA); chromated copper borate (CBC); ammoniacal copper arsenate (ACA); ammoniacal copper zinc arsenate (ACZA); copper chromium fluoride (CFK); copper chromium fluoroborate (CCFB); copper chromium phosphorous (CCP); propiconazole tebuconazole; organo-chloride such as pentachlorophenol (PCP); quaternary ammonium compounds (MC); copper 8-hydroxyquinoline or copper oxene; tri-n-butyltin oxide (TBTO); tri-n-butyltin naphthenate (TBTN); didecyldimethylammonium bromide (DDAB); didecyldimethylammonium chloride (DDAC); silver ions, mercury ions, carbamates, isothiazolones, chlorinated phenoxy and polyhexamethylene beguanidide hydrochlorides, barium metaborate monohydrate, borate salts and mixtures thereof. Preferred compositions of the present invention are water insoluble and comprise inorganic biocides.

In another embodiment of the present invention the composition of the present invention may further comprise about 1 to about 90% by weight of at least one emulsion and/or re-dispersible powder polymer having an average particle size ranging from about 0.3 to about 9 microns wherein more than about 90% by volume of said re-dispersible powder particles are less than or equal to about 400 μm. The terms "re-dispersible polymer powder" and "emulsion polymer" in the context of this formulation are intended to include, but are not limited to, acrylic, SBR, silicons, polyurethane dispersions, polyurethane, alkyl carboxylic acid vinyl ester monomers, branched and unbranched alcohol(meth)acrylic acid ester monomers, vinyl aromatic monomers, olefin monomers, diene monomers and vinyl halide monomers, vinyl ethylene ester and ethylene, vinyl laurate vinyl chloride copolymers, vinyl ester monomers, (meth)acrylate monomers, vinyl aromatic monomers, olefin monomers, 1,3-diene monomers, vinyl halide monomers, homopolymers or copolymers derived from one or more monomers selected from the group consisting of vinyl acetate, vinyl esters of .alpha.-branched monocarboxylic acids having from 9 to 11 carbon atoms, vinyl chloride, ethylene, methyl acrylate, methyl methacrylate, ethyl acrylate, ethyl methacrylate, propyl acrylate, propyl methacrylate, n-butyl acrylate, n-butyl methacrylate, 2-ethylhexyl acrylate, and styrene. and hydrophobic re-dispersible polymer powders compatible with cement binders.

In yet another embodiment of the present invention, the composition may further comprise about 0.1 to about 10% by weight of at least one plasticizer and/or super-plasticizer. The terms "plasticizer and/or superplasticizer" in the context of this formulation is intended to include, but is not limited to polymerized melamine sulfonate, lignin sulfonates, polycarboxylates, poly(meth)acrylates.

In yet still another embodiment of the present invention the composition of the present invention may further comprises about 0.1 to about 20% by weight of pozzolans. The term "pozzolans" in the context of this formulation is intended to include, but is not limited to fly ash, slag, diatomaceous earth, silica fume, calcined shale, metakaolin, rice husk ash, natural pozzolans, and mixtures thereof. The term "fly ash" generally refers to a solid powder having a chemical composition similar to or substantially the same as the composition of the material that is produced during the combustion of powdered coal. This material typically comprises from 25% to about 60% silica, from 10% to about 30% $AL_2O_3$, from 5% to about 25% $Fe_2O_3$, from 0% to about 20% CaO, and from 0% to about 5% MgO. Fly ash particles are typically spherical, ranging in diameter from 1 to 45 microns. In the cementitious composition, the proportion of fly ash comprising particles of less than 45 microns and greater than 10 microns in size is preferably between 5% and around 4% more preferably between 10% and around 35%, and most preferably between 15% and around 30% by weight, based on the total dry ingredients. The proportion of fly ash comprising particles of less than 110 microns in size in the composition is preferably between 1% and around 25%, more preferably between 5% and around 20% and most preferably between 10% and around 15% by weight, based on the total dry ingredients. Class F fly ash greatly reduces the risk of expansion due to sulfate attack.

In another embodiment, a mixture of the re-dispersible polymer powders and emulsion polymers described above can be prepared without the cementious ingredient, which can be added at a later time. For example, one embodiment of the this mixture comprises about 1 to about 90% by weight of at least one emulsion and/or re-dispersible powder polymer having an average particle size ranging from about 0.3 to about 9 microns wherein more than about 90% by volume of said re-dispersible powder particles are less than or equal to about 400 μm. The re-dispersible polymer powder and emulsion polymer can be selected from the group consisting essentially of acrylic, SBR, silicons, polyurethane dispersions, polyurethane, alkyl carboxylic acid vinyl ester monomers, branched and unbranched alcohol(meth)acrylic acid ester monomers, vinyl aromatic monomers, olefin monomers, diene monomers and vinyl halide monomers, vinyl ethylene ester and ethylene, vinyl laurate vinyl chloride copolymers, vinyl ester monomers, (meth)acrylate monomers, vinyl aromatic monomers, olefin monomers, 1,3-diene monomers, vinyl halide monomers, homopolymers or copolymers derived from one or more monomers selected from the group consisting of vinyl acetate, vinyl esters of .alpha.-branched monocarboxylic acids having from 9 to 11 carbon atoms, vinyl chloride, ethylene, methyl acrylate, methyl methacrylate, ethyl acrylate, ethyl methacrylate, propyl acrylate, propyl methacrylate, n-butyl acrylate, n-butyl methacrylate, 2-ethylhexyl acrylate, styrene, hydrophobic re-dispersible polymer powders compatible with cement binders and mixtures thereof. This mixture can be prepackaged with instructions for mixing with the re-dispersible polymer powders and emulsion polymers mixture with the proper type and amount of cement on site. Once mixed, water can be added and the product applied as described below. Shipping the re-dispersible polymer powder and emulsion polymer mixture without the added cement is lower but it is essential that the mixture of these ingredients with cement be precise in order to obtain the benefits of the coating. Therefore, the complete mixture including the cement is preferred so that the proper ratios of ingredients are assured when mixed under controlled conditions in the factory instead on a job site. Other pre-mixes can be made according to the disclosure described herein.

Other embodiments of the composition of the present invention may include in addition to the various components discussed above about 0.5% to about 10% by weight of expansion additives, about 10% by weight of one or more additives selected from the group consisting of flame retardants, pigments, dyes, colorants, stabilizers, ultraviolet light absorbers, antioxidants, insect repellants and mixtures thereof. Pigments that can be used include, without limitation, inorganic pigments such as carbon black, graphite, expandable graphite, zinc oxide, titanium dioxide, and iron oxide, organic pigments, such as quinacridone reds, violets, copper phthalocyanine blues, greens and mixtures thereof.

The present invention is also directed to a method for coating a surface with a least one of the compositions of the present invention described above. The method of the present invention comprises preparing a surface to be coated with at least one of the compositions of the present invention and coating the prepared surface with the composition. The coating can be applied to the prepared surface by trowel, Spackle knife, brush, spray or hopper gun, or any other application device commonly used in the plastering, masonry or painting trades.

The preparation of the surface to be coated depends on materials in which the surface is constructed, the condition of the surface prior to preparation, and the location of the surface to be coated (either inside or outside of the building). If the surface is in relatively good condition or has been recently coated with traditional or modern stucco preparation of the surface for coating comprises applying a primer to the substantially flat continuous surface to produce a primed surface. Then, at least one of the compositions of the present invention can be applied to the prepared surface to produce a finished surface.

In the event that the surface needs to be coated with a masonry mixture, such as stucco or a stucco-like material prior to applying at least one of the compositions of the present invention, the preparation of the surface may include all or part of the following procedures. Affixing at least one water-resistive and drainage barrier material to a surface to produce a protected surface; fastening a wire lath to the protected surface to produce a reinforced surface providing mechanical bond for the stucco to adhere thereto; and applying a construction grade material, such as One Coat Stucco, to said wire lath to produce said substantially flat continuous surface. The wire lath may be constructed from 20 gauge galvanized steel having a diamond pattern, or any other gauge and type of metal, plastic, man-made material used to prepare surfaces for a masonry material. The material applied to the lath can be selected from the group consisting of a cement containing material, traditional or modern stucco, plaster, mortar, or any other material used in the masonry trade. These materials can be applied in a thickness of about ⅜-to about 1 inch thick in order to prepare the surface for application of at least one composition of the present invention.

The composition of the present invention can be applied to prepared surface in a thickness of up to about 3 mm, preferable about 1.5 mm of an inch and more preferable about 1 mm. The thickness in which the composition is applied depends on the surface being coated as well as the purpose for the coating i.e. esthetic only, and/or water-shedding (hydrophobic properties) and/or increased strength. In order to assure maximum waterproofing, prior to and/or after application of the composition of the present invention a sealant material can be applied to joints, turns, around windows and/or door jams as well as pipes and vents so as provide sealant properties to said joints.

As with many masonry products, a skilled tradesman is recommended but a mechanically equipped non-tradesman may also be able to apply the compositions of the present invention using the methods of the present invention. The following example is provided to demonstrate the characteristics, attributes and unexpected results of one embodiment of the present invention and is not offered so as to be limiting on the present invention.

All in all, the composition of the present invention has many favorable characteristics over traditional Stucco and/or Exterior Insulation and Finishing System (EIFS). A chart comparing the characteristics of traditional Stucco, EIFS and the composition of the present invention is provided below. As can bee seen from this chart not only does the product of the present invention not produce VOCs, which makes it less hazardous for the worker, user and environment, but it also possesses many more favorable characteristics than these two popular surfaces.

| PERFORMANCE PROPERTY | COMPOSITION OF THE PRESENT INVENTION | EIFS | TRADITIONAL STUCCO |
|---|---|---|---|
| Green Technology | Exceeds Industry Standard | Below Industry Standard | Exceeds Industry Standard |
| Green Packaging | Exceeds Industry Standard | Below Industry Standard | Exceeds Industry Standard |
| Flame and Smoke Resistance | Exceeds Industry Standard | Below Industry Standard | Exceeds Industry Standard |
| Impact Resistance | Exceeds Industry Standard | Below Industry Standard | Exceeds Industry Standard |
| UV Degradation Yellowing | Exceeds Industry Standard | Below Industry Standard | Exceeds Industry Standard |
| Longevity | Exceeds Industry Standard | Unstable | Exceeds Industry Standard |
| Dirt Pickup Resistance | Exceeds Industry Standard | Costly - extra | Below Industry Standard |
| Elastomeric | Exceeds Industry Standard | Costly - extra | Below Industry Standard |
| Anti-Microbial Protection | Exceeds Industry Standard | Costly - extra | Below Industry Standard |
| Crack Resistance | Exceeds Industry Standard | Exceeds Industry Standard | Below Industry Standard |
| Ease of Spread | Exceeds Industry Standard | Exceeds Industry Standard | Below Industry Standard |
| No Misting Required | Exceeds Industry Standard | Exceeds Industry Standard | Below Industry Standard |
| Color Tinting on Site | Exceeds Industry Standard | Exceeds Industry Standard | Below Industry Standard |
| Real vs. Synthetic Appearance | Exceeds Industry Standard | Below Industry Standard | Exceeds Industry Standard |
| Wastage/Droppage | Exceeds Industry Standard | Below Industry Standard | Below Industry Standard |
| Extended Winter Application | Exceeds Industry Standard | Below Industry Standard | Below Industry Standard |
| Yield per Unit | Exceeds Industry Standard | Below Industry Standard | Below Industry Standard |
| Low Freight Cost | Exceeds Industry Standard | Below Industry Standard | Below Industry Standard |
| Lowest Installed Cost | Exceptional | Below Industry Standard | Below Industry Standard |

Test Methodology

A coating containing a biocide was prepared and placed on a surface according to the method of the present invention. The coating composition has a density of about 10-13 lbs per gallon (differentiating from light weight compositions of much lower densities) and can be applied at thicknesses ranging from 1 to 2 mils up to about 60 mils (differentiating from thick plastering such as stucco that are typically applied at thicknesses in excess of 125 mils). The composition of matter described in this invention consists of:

a hydraulic cement, a polymer in the form of emulsion or redispersible powder and an insoluble inorganic biocide for longer than the state of the art antimicrobial protection. Due the water insoluble nature of the specific biocide described, it cannot be extracted from the coating composition by outdoor exposure. Such biocide being inorganic in nature prevents molecular degradation upon exposure to the UV rays from the sun. The fundamentally inorganic nature of this coating composition prevents any significant deterioration to take place upon outdoor exposure. The coated article was then tested for the effectiveness of biocide in coatings by subjecting the coated article to advance weathering conditions and then evaluating their antimicrobial properties. From the data generated below we have demonstrated that the coating compositions described in this invention have unusual and unpredicted long term durability and antimicrobial protection when compared to state of the art technologies. The results of the testing are presented in the table directly below.

| Coating Composition | Measure of outdoor durability Time in weatherometer before failure | Long term Antimicrobial protection Time in weatherometer when microbial appeared |
|---|---|---|
| Commercial coating #1 w/o Biocide | 1000-3000 hrs | <500 hrs |
| Commercial coating #2 w/normal Biocide | 1000-3000 hrs | 1000-3000 hrs |
| Cement coating #1 w/o polymer and Biocide | Such coatings are impossible to make due to the nature of sand and cement | |
| Commercial coating #3 w polymer and w/o Biocide | >3000 hrs | 500-1000 hrs |
| Commercial coating #4 w polymer and with normal Biocide | >3000 hrs | 1000-3000 hrs |
| Composition #1 of this Invention | >3000 hrs | >3000 hrs |
| Composition #2 of this Invention | >3000 hrs | >3000 hrs |

CONCLUSIONS

This data demonstrates that the compositions described herein raise the state of the art in antimicrobial protections of coatings in that the effectiveness of the biocide remains in the coating of the present invention for at least five (5) years and maybe more depending on the weathering of the coated surface.

The compositions and methods of the present invention can be used and include all types of exterior and interior coatings including EIFS (exterior insulating finishing systems), One Coat Stucco Systems or other cladding systems such as panels etc. The present invention is also directed to coated articles that include structural, construction and ornamental articles coated with the present invention.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A composition for use in construction comprising:
   about 5 to about 95% by weight of dry cement with the remainder of the composition comprising particles having a bulk density greater than about 8 pounds/gal;
   said particles comprising about 0.10 to about 20% by weight of at least one dry thickening agent;
   about 0.10 to about 95.0% by weight of a particulate having an average particle size of about 10 microns to about 3 mm; and
   about 0.10 to about 10.0% by weight of an antimicrobial and/or biocide material wherein the sum of said dry cement and said particles does not exceed 100% by weight.

2. The composition of claim 1 wherein said particles further comprises about 1 to about 90% by weight of at least one emulsion and/or redispersible powder polymer having an average particle size ranging from about 0.3 to about 9 microns wherein more than about 90% by volume of said re-dispersible powder particles are less than or equal to about 400 μm.

3. The composition of claim 2 wherein said particles further comprises about 0.1 to about 10% by weight of at least one plasticizer and/or super-plasticizer.

4. The composition of claim 3 further comprising about 0.1 to about 20% by weight of pozzolans.

5. The composition of claim 4 wherein said particles further comprises about 0.5% to about 10% by weight of expansion additives.

6. The composition of claim 5 wherein said particles further comprises up to about 10% by weight of one or more additives selected from the group consisting of flame retardants, pigments, dyes, colorants, stabilizers, ultraviolet light absorbers, antioxidants, insect repellants and mixtures thereof.

7. The composition of claim 6 wherein said pigments include, without limitation, inorganic pigments selected from the group consisting of carbon black, graphite, expandable graphite, zinc oxide, titanium dioxide, and iron oxide, organic pigments, selected from the group consisting of quinacridone reds, violets, copper phthalocyanine blues, greens and mixtures thereof.

8. The composition of claim 1 wherein said one or more thickening agent is selected from the group consisting of cellulose ether, modified cellulose ether, polyvinyl alcohol acetylated hydrophobically modified polyvinyl alcohol and mixtures thereof.

9. The composition of claim 1 wherein said antimicrobial or biocide material is selected from the group consisting of fungicides, herbicides, insecticides, antimicrobial agents can include sodium, potassium, calcium, zinc, copper, and barium salts of carbonate, silicate, sulfate, halide, and borate in all forms; zinc carboxylates; boric acids; sodium dichromate; copper chrome arsenate (CCA); chromated copper borate (CBC); ammoniacal copper arsenate (ACA); ammoniacal copper zinc arsenate (ACZA); copper chromium fluoride (CFK); copper chromium fluoroborate (CCFB); copper chromium phosphorous (CCP); propiconazole tebuconazole; organo-chloride such as pentachlorophenol (PCP); quaternary ammonium compounds (AAC); copper 8-hydroxyquinoline or copper oxene; tri-n-butyltin oxide (TBTO); tri-n-butyltin naphthenate (TBTN); didecyldimethylammonium bromide (DDAB); didecyidimethylammonium chloride (DDAC); silver ions, mercury ions, carbamates, isothiazolones, chlorinated phenoxy and polyhexamethylene beguanidide hydrochlorides, barium metaborate monohydrate, borate salts and mixtures thereof.

10. The composition of claim 2 wherein said one or more redispersible powder polymers is selected from the group consisting of acrylics, silicons, polyurethane dispersions, polyurethane, alkyl carboxylic acid vinyl ester monomers, branched and unbranched alcohol(meth)acrylic acid ester monomers, vinyl aromatic monomers, olefin monomers, diene monomers and vinyl halide monomers.

11. The composition of claim 10 wherein said emulsion can be an acrylic or SBR and at least one re-dispersible powder polymer, copolymer or terpolymer is selected from the group consisting of vinyl ethylene ester and ethylene, vinyl laurate vinyl chloride copolymers, vinyl ester monomers, (meth)acrylate monomers, vinyl aromatic monomers, olefin monomers, 1,3-diene monomers, vinyl halide monomers, homopolymers or copolymers derived from one or more monomers selected from the group consisting of vinyl acetate, vinyl esters of .alpha.-branched monocarboxylic acids having from 9 to 11 carbon atoms, vinyl chloride, ethylene, methyl acrylate, methyl methacrylate, ethyl acrylate, ethyl methacrylate, propyl acrylate, propyl methacrylate, n-butyl acrylate, n-butyl methacrylate, 2-ethylhexyl acrylate, and styrene and hydrophobic re-dispersible polymer powders compatible with cement binders.

12. The composition of claim 3 wherein said plasticizer and/or superplasticizer is selected from the group consisting of polymerized melamine sulfonate, lignin sulfonates, polycarboxylates, poly(meth)acrylates.

13. The composition of claim 3 wherein said one or more pozzolans is selected from the group consisting of class C fly ash, class F fly ash, slag, diatomaceous earth, silica fume, calcined shale, metakaolin, rice husk ash, natural pozzolans, and mixtures thereof.

14. A method for coating a surface with a composition of claim 1 comprising preparing said surface for coating with said composition; and coating said surface with said composition.

15. The method of claim 14 wherein preparing said surface for coating comprises applying a primer to a substantially flat continuous surface to produce a primed surface; and
    applying said composition to said primed surface to produce a finished surface.

16. The method of claim 15 wherein said substantially flat continuous surface is produced by adhering at least one water-resistive and drainage barrier material to a surface to produce a protected surface;
    fastening a wire lath to said protected surface to produce a reinforced, mechanically bondable surface; and
    applying a construction grade material to said wire lath to produce said substantially flat continuous surface.

17. The method of claim 16 wherein the wire lath is made from 20 gauge galvanized steel having a diamond pattern.

18. The method of claim 17 where in said construction grade material applied to said wire lath is a cement containing material.

19. The method of claim 18 wherein the cement containing material is a stucco material and is applied in a thickness of about ⅜-1 inch thick.

20. The method of claim 16 further comprising applying a sealant material to areas wherever said construction grade material meets another material to produce a joint so as provide sealant properties to said joints.

21. An exterior building surface coated with the composition of claim 1.

* * * * *